United States Patent
Benje et al.

(10) Patent No.: US 6,437,204 B1
(45) Date of Patent: Aug. 20, 2002

(54) PROCESS FOR THE VCM PRODUCTION

(75) Inventors: Michael Benje, Darmstadt; Thomas Schubotz, Bad Soden; Hartmut Schön, Oberursel, all of (DE)

(73) Assignee: Krupp Uhde GmbH, Dortmund (DE)

( * ) Notice: Subject to any disclaimer, the term of this patent is extended or adjusted under 35 U.S.C. 154(b) by 0 days.

(21) Appl. No.: 09/524,658

(22) Filed: Mar. 13, 2000

(30) Foreign Application Priority Data

Dec. 3, 1999 (DE) .......................... 199 11 078

(51) Int. Cl.⁷ ................................ C07C 17/15

(52) U.S. Cl. ....................... 570/243; 570/224

(58) Field of Search ................. 570/224, 243

(56) References Cited

U.S. PATENT DOCUMENTS 4,044,068 A * 8/1977 Kurtz .......................... 570/224
4,051,193 A * 9/1977 Kurtz et al. ................ 570/224

* cited by examiner

*Primary Examiner*—Alan Siegel
(74) *Attorney, Agent, or Firm*—Katten Muchin Zavis Rosenman

(57) ABSTRACT

In a process for the production of VCM, the gaseous reactants and an inert carrier gas are fed into an adiabatic reaction zone in the oxychlorination section, both reaction zones being associated with an integral fluidised bed, the cooled reaction zone containing a vertically coaxial hollow cooling rod bundle forming a passage. A balanced production of VCM is to be achieved, this being done by selecting a ratio of 1 to 6 inclusive between the equivalent diameter of the passage cross-sectional area and the mean gas bubble pocket diameter of the fluidised bed.

5 Claims, 2 Drawing Sheets

PROCESS FOR THE VCM PRODUCTION

FIELD OF INVENTION

The present invention relates to a method of producing monomer vinyl chloride (VCM), wherein a balance is maintained between the hydrogen chloride (HCl) produced and consumed in the various reactions.

The process for the production of VCM with a adequate HCl balance, hereinafter referred to as "balanced VCM process", comprises the following process steps:

direct chlorination in which part of the required intermediate product 1,2-dichloroethane is produced from ethylene ($C_2H_4$) and chlorine ($Cl_2$);

oxychlorination in which the other part of the required intermediate product 1,2 dichloroethane is produced from ethylene, hydrogen chloride (HCl) and oxygen ($O_2$);

EDC purification in which the by-products generated in the oxychlorination and EDC pyrolysis sections are removed from both partstreams of the intermediate EDC product and from the EDC recycled from the fractionation section in order to obtain a so-called crackable EDC suitable for use in the pyrolysis section;

EDC pyrolysis in which the crackable EDC is cracked thermally, thus basically yielding VCM, HCl and non-reacted EDC in the cracked gas plus some additional co-products; and fractionation in which the desired pure EDC product is separated from the cracked gas while simultaneously recovering useful substances (HCl and non-reacted EDC) contained in the cracked gas, these substances being recycled in the balanced VCM process.

BACKGROUND OF THE INVENTION

In a commercial-scale plant operating by the balanced VCM process, the oxychlorination of ethylene proceeds preferably in a catalytically acting fluidised bed. Publication (McPherson, R. W. et al., "Vinyl Chloride Monomer . . . What You Should Know", Hydrocarbon Processing, $58^{th}$ edition, March 1979, page 75–88) explains that the reaction temperature may not exceed 325° C., because the amount of by-products obtained could otherwise become unreasonably high.

The oxychlorination of ethylene is a distinctively exothermal reaction. Because of the limited temperature range of the reaction, it is imperative that the generated heat be dissipated directly. Hence, the fluidised bed is normally brought into contact with suitable surfaces, the purpose of which is to effectively extract heat from the fluidised bed.

The heat-extracting surfaces and the other surface in contact with the material of the fluidised bed are subject to wear as a result of the fact that the fluidised bed material contains corundum. These surfaces are also likely to corrode, because one of the gaseous reaction products in the fluidised bed is hydrogen chloride that forms on the surfaces.

It is known from GB-PS 1 100 439 (Harping et al. ) that a copper catalyst on a corundum ($Al_2O_3$) carrier is used for the oxychlorination of ethylene. The bulk catalytic material used in the fluidised bed has a copper content of about 10% (wt).

NL-PS 65/06985 states that the catalytically acting copper impregnate is deposited on spherical particles of corundum, thus permitting a copper content of about 10% (wt) to be adjusted. The size of the corundum particles is in the order of 20 $\mu$m to 200 $\mu$m.

It can further be seen from U.S. Pat. No. 3,488,398 (Harping et al.) that the catalytically acting copper impregnate used is in the form of copper halides, preferably copper chloride. It is stated that a copper content of 3% (wt) to 12% (wt) is practicable, but that copper contents of more than 12% (wt) can also be used, although this is not expedient, because the reaction yield cannot be increased by this method and the catalytically acting fluidised bed tends to cause incrustations in the oxychlorination reactor to an increasing extent.

Since the introduction of the balanced VCM process, a number of proposals have therefore been made for reducing the production of detrimental by-products in the oxychlorination reactor while simultaneously permitting the reactor to operate reliably without any fouling by incrustations and reducing the inherent abrasion and/or corrosion to a reasonable level.

Published patent application WO 96/26 003 (Krumbock) describes an oxychlorination reactor in which a reactant gas stream is fed into the fluidised bed in counter-current to the fluidising gas stream flowing in an upward direction. The primary purpose of this arrangement is to reduce or eliminate abrasion.

All operators of VCM plants using the balanced VCM process require that these plants be such that they are able to produce VCM during prolonged periods without any standstills caused by the particular operating conditions or malfunctions. The requirement for oxychlorination reactors is that a stable temperature range be achieved and maintained in the fluidised bed over prolonged periods even when the grain size spectrum of the fluidising bulk material, which consists of spherical particles of corundum, shifts to lower values due to abrasion.

The average grain size of fresh fluidising bulk material is in the order of 50 $\mu$m to 60 $\mu$m. Due to abrasion, the grain size gradually decreases to particle sizes of 30 $\mu$m to 40 $\mu$m.

SUMMARY OF THE INVENTION

The aim of the present invention is, therefore, to define a balanced process for the production of VCM, comprising the steps of:

(a) feeding gaseous reactants and an inert carrier gas to an adiabatic reaction zone in an oxichlorination section;

(b) transferring the gases and the portion of the gaseous reaction products formed in the adiabatic reaction zone to a cooled reaction zone arranged above the adiabatic reaction zone and converting the remainder of the reactant, wherein both reaction zones are associated with an integral bed which is fluidised by the gases and in which the catalytic reaction takes place; and (c) withdrawing the gaseous reaction product from the fluidised bed in an upward direction, wherein the cooled reaction zone contain a vertically coaxial hollow cooling rod bundle which forms a passage, the hollow cooling rods of which being almost equidistantly spaced, wherein the part of the fluidised bed that is arranged in the cooled reaction zone is exposed to the heat-dissipating surfaces of the hollow cooling rods and the fluidising bulk material, the gases being conducted through the passages between the hollow cooling rods in a manner which permits dissipation of their heat, and wherein the ratio of the equivalent diameter representing the passage cross-sectional area to the mean gas bubble pocket diameter of the fluidised bed is 1 to 6 inclusive.

DETAILED DESCRIPTION OF THE PREFERRED EMBODIMENTS

In a process for the production of VCM, the gaseous reactants and an inert carrier gas are fed into an adiabatic reaction zone in the oxychlorination section, these gases and the gaseous reaction products obtained in the adiabatic reaction zone being transferred to a cooled reaction zone arranged above the adiabatic reaction zone and required to convert the remainder of the reactant. Both reaction zones are associated with an integral fluidised bed, which is fluidised by the said gases, in which the catalytic reaction takes place with the aid of the fluidising bulk material and from which the reaction product and the carrier gas are withdrawn in gaseous state at the top of the fluidised bed. The cooled reaction zone is penetrated by a vertically coaxial hollow cooling rod bundle, which forms a passage and the hollow cooling rods of which are spaced almost equidistantly. The part of the fluidised bed that is located in the cooled reaction zone is exposed almost completely to the hollow cooling rod surfaces, the fluidising bulk material and the gases being routed through the passages between the hollow cooling rods so as to dissipate heat. The above aim is achieved by selecting a ratio (of 1 to 6 inclusive) between the cross-sectional area of the passages between the hollow cooling rods and the average equivalent gas bubble pocket diameter of the fluidised bed.

The hollow cooling rods can be arranged in a rectangular or triangular 60° pitch in the rod bundle.

A cross-sectional passage in the hollow cooling rod bundle is filled with the fluidising bulk material and the gases and is enclosed by the system lines of the pitch. The cross-sections of the hollow cooling rods are also located in the square or triangle enclosed by the system lines (FIG. 2a/3a). The free cross-section of a passage filled with the fluidising bulk material and gases has an area with a polygonal perimeter.

In order to be able to describe the surface area of such a polygon with a single dimension, as is the case with a circular area (for a circular area this dimension is the circle diameter), a so-called equivalent diameter is used as the descriptive dimension. The equivalent diameter is defined as the quotient between the quadruple of the free overall cross-sectional area and the circumference of the free surface area.

The average gas bubble pocket diameter of the fluidised bed is determined mathematically from the process variables defining the properties of the fluidised bed. The models and relationships drawn up by J. Werther and published in the encyclopaedia ("Ullmanns Enzyklopädie der technischen Chemie", 4$^{th}$ edition (1975), volume 9, page 448, FIG. 16) are used for this purpose. In the following, the equations are described, with the aid of which the gas bubble pocket diameter can be determined.

The gas bubble pocket growth and decay in fine-grained fluidised layers (Geldart group A) can be described by the following differential equation:

$$\frac{d}{dh}d_v = \underbrace{\left(\frac{3\varepsilon_b}{9\pi}\right)^{\frac{1}{3}}}_{\text{gas bubble pocket growth}} - \underbrace{\frac{d_v}{3\lambda u_b}}_{\text{decay mechanism}} \tag{1}$$

where $$\frac{d}{dh}d_v$$

=Variation of the gas bubble pocket diameter with the fluidised bed depth (for Geldart group A≈0, i.e. gas bubble pocket diameter=constant)

$d_v$=bubble diameter [m]

$\varepsilon_b$=bubble pocket volume portion in the fluidised bed $\lambda$=Mean bubble lifetime between two decay processes.

A) Lambda (mean bubble lifetime between two decay processes estimated according to ("Ullmann's Encyclopedia of Industrial Chemistry", VCH, Weinheim, 1992, volume B4, page 248)

$$\lambda = 280 \cdot \frac{u_{mf}}{g} \tag{2}$$

where $\mu_{mf}$ [m/s] is the minimum fluidisation velocity and g [9.81 m/s$^2$] is the acceleration due to gravity.

B) The Reynolds number and, consequently, the velocity at minimum fluidisation were estimated according to Wen and Yu (C. Y. Wen and Y. H. Yu, AICHE J.4 (1958), page 15):

$$Re_{mf} = [3 \; 3.7^2 + 0.040 \; 8Ar]^{0.5} - 33.7 \tag{3}$$

where

Ar is the Archimedes number for the respective mean particle diameter in the fluidised bed, $$Ar = \frac{g \cdot d_p^3}{v} \cdot \frac{\rho_s \rho_f}{\rho_f}$$

and $d_p$=particle diameter in m
$\rho_s$=catalyst density 3100 kg/m$^3$
$\rho_f$=gas density 4.3 kg/m$^3$
$v$=kinetic viscosity of the gas 5.4·10$^{-6}$ m$^2$s.

If $d_p$=38.3 μm, 35.3 μm, 40.3 μm (measured in running reactors), then $u_{mf}$=0.0012 m/s, 0.001 m/s, 0.0013 m/s.

C) The gas bubble pocket volume portion of the fluidised bed is calculated according to ("Ullman's Encyclopedia of Industrial Chemistry", VCH, Weinheim, 1992, volume B4, page 248)

$$\varepsilon_b = \frac{V_b}{U_b} \tag{4}$$

where $V_b$=0.8 (u−$u_{mf}$)

u=free flow gas velocity=total gas volume/free cross-sectional area of reactor [m/s]; in this case: 0.369 m/s V=gas bubble pocket volumetric flow rate (in terms of velocity referred to the free cross-sectional area of the reactor)

$U_{mf}$=gas velocity at minimum fluidisation and $$U_b = V_b + 0.71 \cdot \Theta \cdot \sqrt{g \cdot d_v} \, [m/s] \tag{5}$$

where $U_b$=velocity of ascending gas bubbles.

The following applies to fine-grain fluidised beds (Geldart group A):

$$\Theta = 3 \cdot 2 d_t^{0.33} \, 0.05 \leq 1m \tag{6}$$

where $d_t$ is the hydraulic diameter of the reactor [m], formed by the reactor inside diameter and the cumulated surface areas of the hollow cooling rod bundle.

Example: $d_t$ (60° pitch)=0.24 m $d_t$ (90° pitch)=0.38 m.

The equilibrium gas bubble pocket diameter can be determined by iteration from the above equations.

To this end, an oxychlorination reactor according to the present invention is represented in FIG. 1. The longitudinal section of the vessel is shown. The hatched reference surface in the lower part of the reactor marks the area of the cooled reaction zone as the centre part. In this area, broken lines represent the centre lines of the hollow cooling rod of the cooling rod bundle inside the reactor.

The adiabatic reaction zone is arranged below the cooled reaction zone. It is located above the dished reactor bottom equipped with inlet nozzles and below the lower horizontal limit of the cooling rod bundle.

When the reactor is in operation, the fluidised bed fills both zones.

The dust removal facilities and the dust recycling tubes are arranged in the upper part of the reactor. This prevents the fine dust fraction of the fluidising bulk material from being entrained by the gases leaving the reactor at the top.

Figure 1:
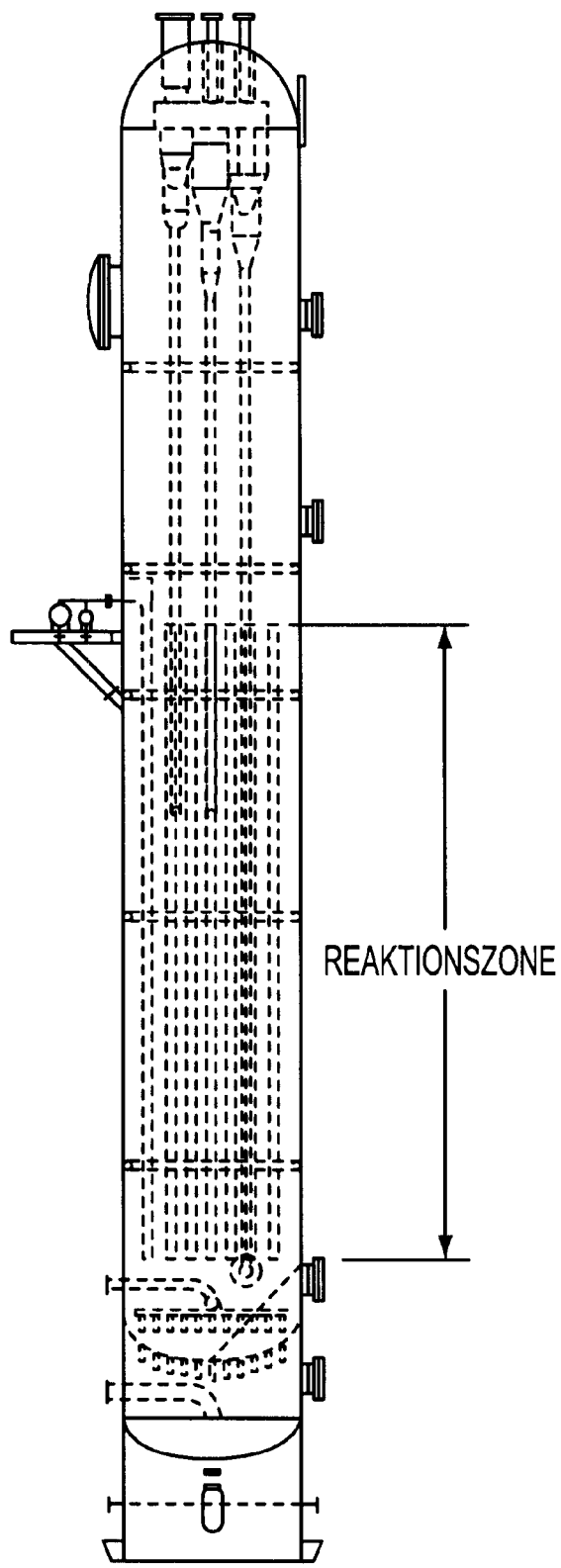
Figure 2:
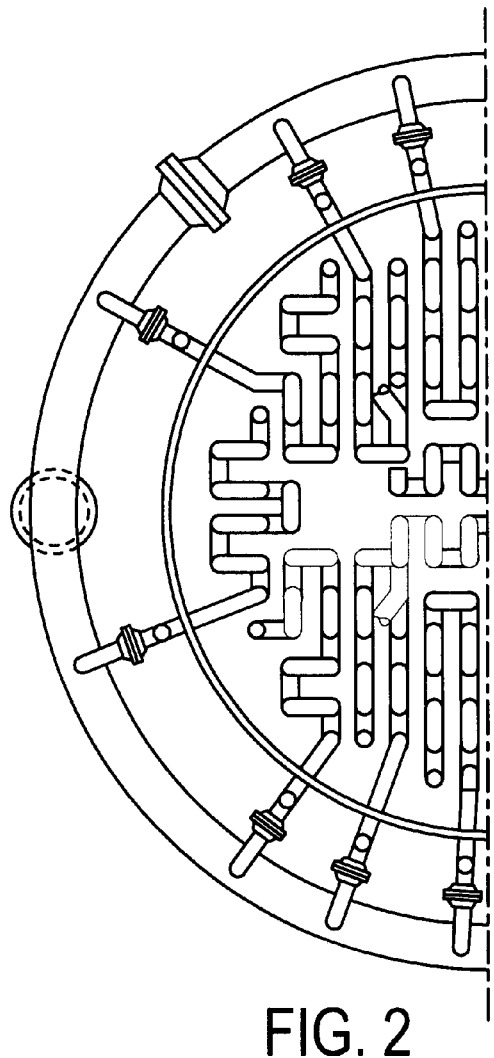
FIG. 2 shows the cross-sectional area of the left half of a reactor with 90° pitch tubular hollow cooling rods of the cooling rods bundle.
Figure 3:
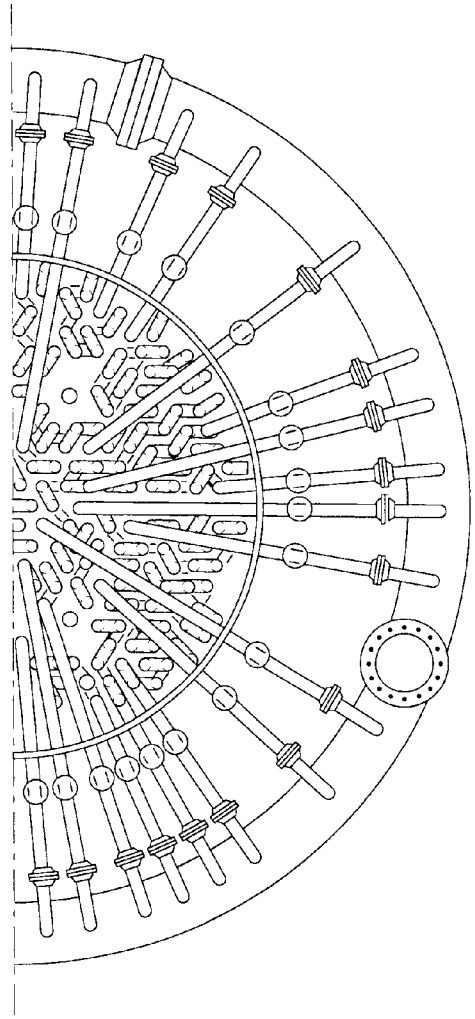
FIG. 3 shows a cross-sectional area of the right half of a reactor with 60° pitch hollow cooling rods of the cooling rods bundle.
Figure 2A:
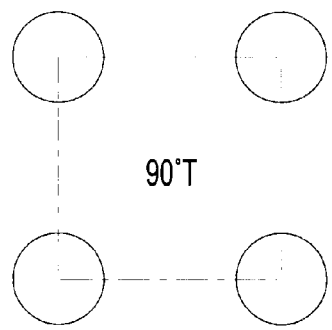
FIG. 2a shows a field (90°T) of the 90° pitch used.
Figure 3A:
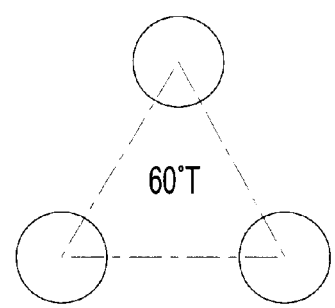
FIG. 3a shows a field (60°T) of the 60° pitch used.

The tube diameter of the hollow cooling rods in FIG. 2 is larger than that of FIG. 3.

The dimensions and process variables of the two examples shown as embodiments of the invention are compared below.

It goes without saying that the cooling rod bundle is not limited to using heat transfer oil as the cooling agent. Likewise, the hollow cooling rods need not be connected on the heat transfer fluid side exclusively in parallel nor exclusively in series; hybrid connections are conceivable, e.g. partial series connection of two or more follow hollow cooling rods to a group and then a parallel connection of these series-connected groups. In heat exchangers, such arrangements are known as alternate tubing area.

It further goes without saying that the invention is not limited to the two examples shown in this application; the comparative table of dimensions and process variables shown below features the 90° pitch in the left-hand column and the 60° pitch in the right-hand column.

| | 90° pitch | 60° pitch |
|---|---|---|
| Cooling tube outside diameter | 114.3 mm | |
| | 88.9 mm | |
| Tube wall spacing in the hollow cooling rod bundle | 88.9 mm | 63 mm |
| λ | 0.034 s | |
| | 0.034 s | |
| | 90° pitch | 60° pitch |
| $U_b$ | 1.18 m/s | |
| | 1.06 m/s | |
| $\epsilon_b$ | 0.23 | 0.28 |
| $D_v$ | 0.031 m | |
| | 0.03 m | |

It can be seen that the bubble pocket size is insignificantly affected by a differing cooling rod geometry and, consequently, by a differing reactor diameter.

A comparison of the heat transfer with different designs of the hollow cooling rod bundle shows surprisingly that the present invention covers a broad spectrum of reactor designs.

Using a formula proposed by Kunii and Levenspiel (D. Kunii and 0. Levenspiel, "Fluidization Engineering", Butterworth-Heinemann 1991, page 329), the following applies to the ratio of the heat transfer coefficient with a 60° pitch to the heat transfer coefficient with a 90° pitch:

$$\frac{\alpha_{bw,60}}{\alpha_{bw,90}} = \sqrt{\frac{f_{w,60}(1-\varepsilon_{bw,60})}{f_{w,90}(1-\varepsilon_{bw,90})}} \tag{7}$$

where $\alpha_{bw}$=heat transfer coefficient between tube wall and fluidized bed (W/m²K)

$f_w$=bubbling frequency (1/s)

$\epsilon_{bw}$=bubble volume portion on the tube surface.

The assumption made for the above is that the thermal conductivity of the emulsion phase and the suspension phase porosity remain unchanged. As the bubble pocket diameters are small in relation to the reactor diameter, it can further be assumed that the ascending bubbles are randomly distributed over the cross-sectional area of the reactor. In this case, the values of $f_w$ and $\epsilon_{bw}$ that apply for the heat exchange surface are substituted by the local bubbling frequency $f_w$ and the local bubble volume portion $\epsilon_b$:

$$\frac{\alpha_{bw,60}}{\alpha_{bw,30}} = \sqrt{\frac{f_{,60}(1-\varepsilon_{b,60})}{f_{,30}(1-\varepsilon_{b,90})}} \tag{8}$$

The bubble frequency is represented by:

$$f = \frac{3}{2} \frac{U_b \varepsilon_b}{d_v} \tag{9}$$

links the local bubbling frequency with the local bubble size, the ascent velocity and the bubble volume portion. Substituting the appropriate values in equation (9) by equation (8) yields:

$$\frac{\alpha_{bw,60}}{\alpha_{bw,90}} = \sqrt{\left(\frac{U_{b,60}}{U_{b,90}}\right) \cdot \left(\frac{d_{v,90}}{d_{v,60}}\right) \cdot \left(\frac{\varepsilon_{b,60}(1-\varepsilon_{b,60})}{\varepsilon_{b,90}(1-\varepsilon_{b,90})}\right)} \tag{10}$$

The values thus calculated for the respective centre of the heat exchanger bundle and

|  | 90° pitch | 60° pitch |
|---|---|---|
| $U_b$ | 1.18 m/s | 1.06 m/s |
| $\epsilon_b$ | 0.23 | 0.28 |
| $d_v$ | 0.031 m | 0.03 m |
| yield | $\dfrac{\alpha_{bw,60}}{\alpha_{bw,90}} = 1.03$ | |

This means that the heat transfer coefficient of a 60° pitch reactor is a somewhat better than that of a 90° pitch reactor. This shows that the present invention permits the provision both of a close compact pitch of the hollow cooling rod bundle and of a relatively wide pitch.

A characteristic diagram defined by several parameters is thus available to the designer of the reactor intervals, from which he can make an optimum selection of the catalyst properties with a view to achieving either a lower incrustation tendency or less abrasion or a low catalyst activity loss, depending on the particular requirements. This is a major and surprising advantage of the invention.

What is claimed is:

1. A process for the production of the intermediate product 1.2 dichloroethane required in the production of VCM with an adequate hydrogen chloride balance, comprising the steps of:

(a) feeding gaseous reactants ethylene, hydrogen chloride and oxygen and an inert carrier gas to an adiabatic reaction zone in an oxichlorination section;

(b) transferring the gases and the portion of the gaseous reaction products formed in the adiabatic reaction zone to a cooled reaction zone arranged above the adiabatic reaction zone and converting the remainder of said the reactant, wherein both reaction zones are associated with an integral and catalytically acting bed which is fluidised by the gases in which the catalytic reaction takes place; and (c) withdrawing the gaseous reaction product from the fluidised bed in an upward direction, wherein the cooled reaction zone contain a vertically coaxial hollow cooling rod bundle which forms a passage, the hollow cooling rods of which being almost equidistantly spaced, wherein the part of the fluidised bed that is arranged in the cooled reaction zone is exposed to the heat-dissipating surfaces of the hollow cooling rods and the fluidising bulk material, the gases being conducted through the passages between the hollow cooling rods in a manner which permits dissipation of their heat, and wherein the ratio of the equivalent diameter representing the passage cross-sectional area to the mean gas bubble pocket diameter of the fluidised bed is 1 to 6 inclusive.

2. The process of claim 9, wherein the hollow cooling rods in the cooling rod bundle are installed in a rectangular arrangement (90° pitch) or in a triangular arrangement (60° pitch).

3. The process of claim 9, wherein heat transfer oil is used as the heat transfer fluid and tube coils conveying the heat transfer oil are used, the spacing between the tube walls and/or between the tube wall and reactor wall being at least the mean equilibrium bubble pocket diameter of the gas flowing through the catalyst bed.

4. The process of claim 9, wherein the heat dissipated in the reactor is sensible heat.

5. The process of claim 9, wherein a catalytic granulate is used that is resistant to caking or incrustation.

* * * * *